(12) United States Patent
Schäfer et al.

(10) Patent No.: US 6,540,749 B2
(45) Date of Patent: Apr. 1, 2003

(54) BONE SCREW

(75) Inventors: Bernd Schäfer, Eggstrasse 27, CH-6315 Oberägeri (CH); Henry Halm, Neustadt (DE)

(73) Assignee: Bernd Schäfer, Oberägeri (CH)

( * ) Notice: Subject to any disclaimer, the term of this patent is extended or adjusted under 35 U.S.C. 154(b) by 0 days.

(21) Appl. No.: 10/066,572

(22) Filed: Feb. 6, 2002

(65) Prior Publication Data

US 2002/0116001 A1 Aug. 22, 2002

(30) Foreign Application Priority Data

Feb. 17, 2001 (DE) .......................... 101 08 065

(51) Int. Cl.⁷ ................................ A61B 17/60
(52) U.S. Cl. .......................... 606/61; 606/73
(58) Field of Search ................ 606/54–62, 72, 606/73

(56) References Cited

U.S. PATENT DOCUMENTS

| | | | | |
|---|---|---|---|---|
| 5,129,388 A | * | 7/1992 | Vignaud et al. | 606/61 |
| 5,176,680 A | * | 1/1993 | Vignaud et al. | 606/61 |
| 5,217,497 A | * | 6/1993 | Mehdian | 623/17 |
| 5,360,431 A | * | 11/1994 | Puno et al. | 606/72 |
| 5,385,583 A | * | 1/1995 | Cotrel | 623/17 |
| 5,443,467 A | * | 8/1995 | Biedermann et al. | 606/65 |
| 5,474,555 A | * | 12/1995 | Puno et al. | 606/73 |
| 5,536,268 A | * | 7/1996 | Griss | 606/61 |
| 5,545,165 A | * | 8/1996 | Biedermann et al. | 606/61 |
| 5,738,685 A | * | 4/1998 | Halm et al. | 606/61 |
| 6,077,262 A | | 6/2000 | Schläpfer | |
| 6,224,598 B1 | * | 5/2001 | Jackson | 606/61 |

FOREIGN PATENT DOCUMENTS

WO    WO 95/01132    *  1/1995

* cited by examiner

Primary Examiner—Ralph A. Lewis
(74) Attorney, Agent, or Firm—Paul Vincent

(57) ABSTRACT

The invention concerns a bone screw comprising a screw shaft and a forked head into which a correction rod can be fixed. The forked head bears a nut which is connected to the forked head by a bayonet joint.

12 Claims, 3 Drawing Sheets

BONE SCREW

This application claims Paris Convention priority of DE 101 08 065 filed Feb. 17, 2001 the complete disclosure of which is hereby incorporated by reference.

BACKGROUND OF THE INVENTION

The invention concerns a bone screw, in particular a pedicle screw, comprising a forked head with a groove for receiving a correction rod, a threaded screw shaft and a nut for the free ends of the forked head.

EP 0 699 055 B1 discloses an osteosynthesis device comprising a bone screw including a forked head into which a correction rod can be inserted. The correction rod is held by a head nut which is screwed onto a thread provided on the legs of the forked head. There are situations when screwing of the head nut can be difficult or e.g. present problems to a surgeon who cannot directly see the screw.

It is therefore the underlying purpose of the invention to further develop a bone screw of the above-mentioned type such that the nut and the forked head can be easily connected even in difficult situations.

SUMMARY OF THE INVENTION

This object is achieved with a bone screw of the above-mentioned type in accordance with the invention in that the free ends of the forked head and the nut form a bayonet joint.

In accordance with the inventive bone screw, the nut is disposed onto the free ends of the two legs of the forked head like a bayonet joint and slightly turned. This bayonet joint has the substantial advantage that the nut must no longer be mounted onto a thread but merely placed on the end of the forked head. This is easy to do even in difficult situations with insufficient sighting.

In a preferred further development, the free ends comprise radially outwardly extending projections. These projections extend through the peripheral length of the free ends of the forked head. This permits transmission of relatively large forces and the surface pressure is relatively small.

In accordance with the invention, the inner circumference of the nut comprises two radially inwardly projecting noses which each extend through 200 to 1200, preferably 850 of the inner periphery. The projections of the free ends of the forked head engage behind these noses to thereby form the bayonet joint.

In a further development, at least one free end of the forked head is provided with an axial extension. This axial extension defines the maximum turning of the nut to close the bayonet joint. Towards this end, the inner surface of the nut has a receiving groove for the extension extending through a portion of the inner circumference. When the nut is disposed onto the ends of the forked head, the extension engages into the receiving groove and the nut can be turned until the extension has reached the end of the receiving groove.

In another embodiment, the inner side of the nut is provided with a stop for the extension. In this embodiment, the stop engages the path of the extension such that the nut can be turned until the extension abuts the stop.

In a further development, the separation between the groove bottom of the forked head and the side of the nut facing the groove is larger than the inside diameter of the forked legs of the forked head, when the nut is disposed onto the forked head. This means that, when the correction rod has been inserted into the forked head and the nut is placed onto the free ends of the forked head, the nut is not supported on the correction rod. It can therefore be easily turned to close the bayonet joint.

In a further development, the nut is provided with a central threaded bore for a screw, in particular, a set screw. The correction rod is fixed in the forked head by this set screw which is screwed into the nut after closing the bayonet joint to press onto the correction rod. The screwed-in end of the set screw preferably comprises a tip or cupped gripping point which penetrates the surface of the correction rod. The set screw maintains the correction rod at the bottom of the forked head and secures the nut on the forked head to keep the bayonet joint in the closed position.

The screwing direction of the set screw preferably corresponds to the turning direction of the bayonet joint such that the nut must not be held when screwing in the set screw. Release of the nut is thereby relatively easy since the screwing direction of the set screw corresponds to the turning direction for opening the bayonet joint.

The outer circumference of the nut is provided with a tool engagement surface for turning the nut, in particular a hexagon, which permits easy movement of the nut in both turning directions to open and close the bayonet joint.

Further advantages, features and specifics of the invention can be extracted from the following detailed description of a particularly preferred embodiment with reference to the drawing. The features in the drawing, in the claims, and the description may be essential to the invention either individually or collectively in any arbitrary combination.

DESCRIPTION OF THE PREFERRED EMBODIMENT

Figure 1:
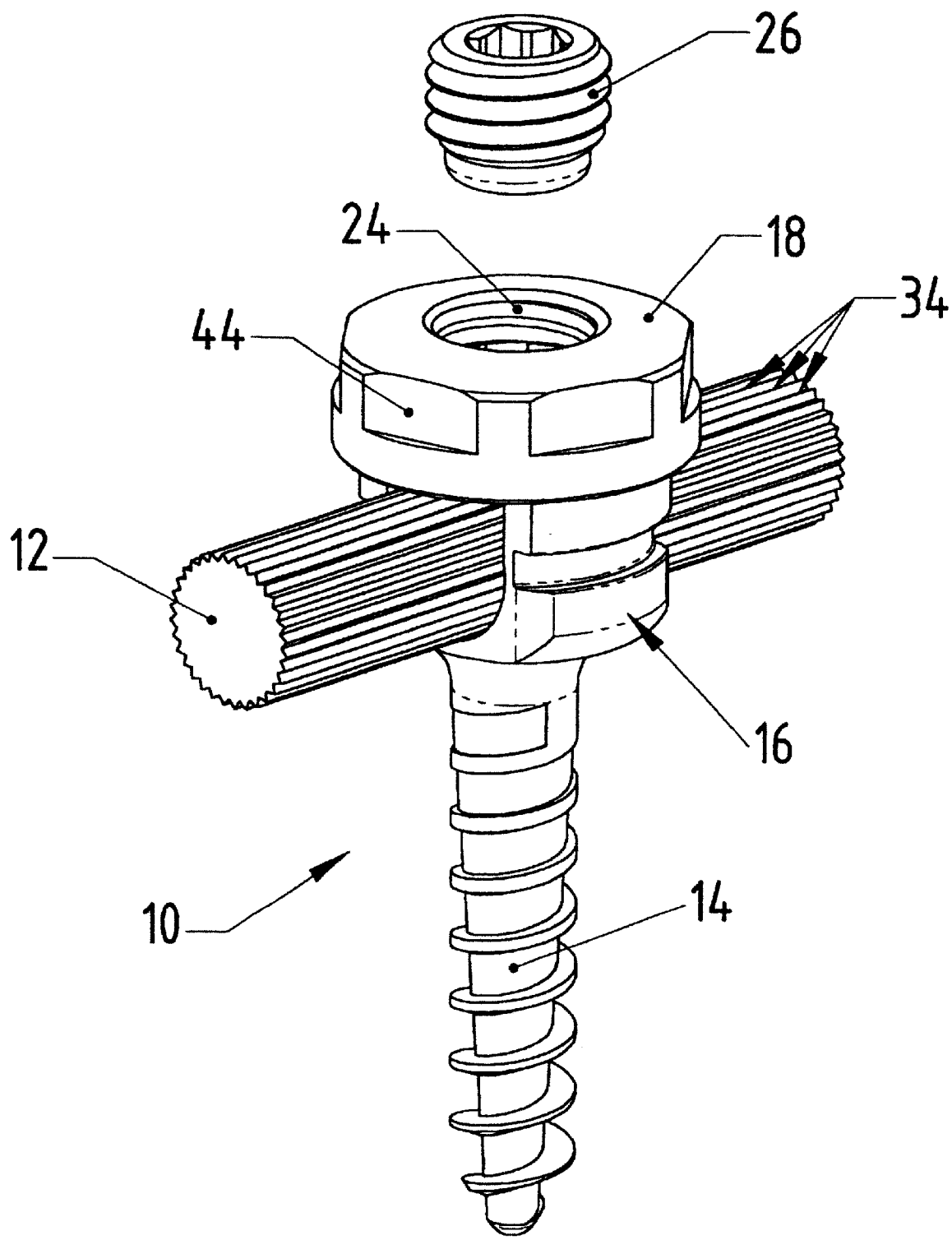
FIG. 1 shows a perspective view of the bone screw including inserted correction rod.
Figure 2:
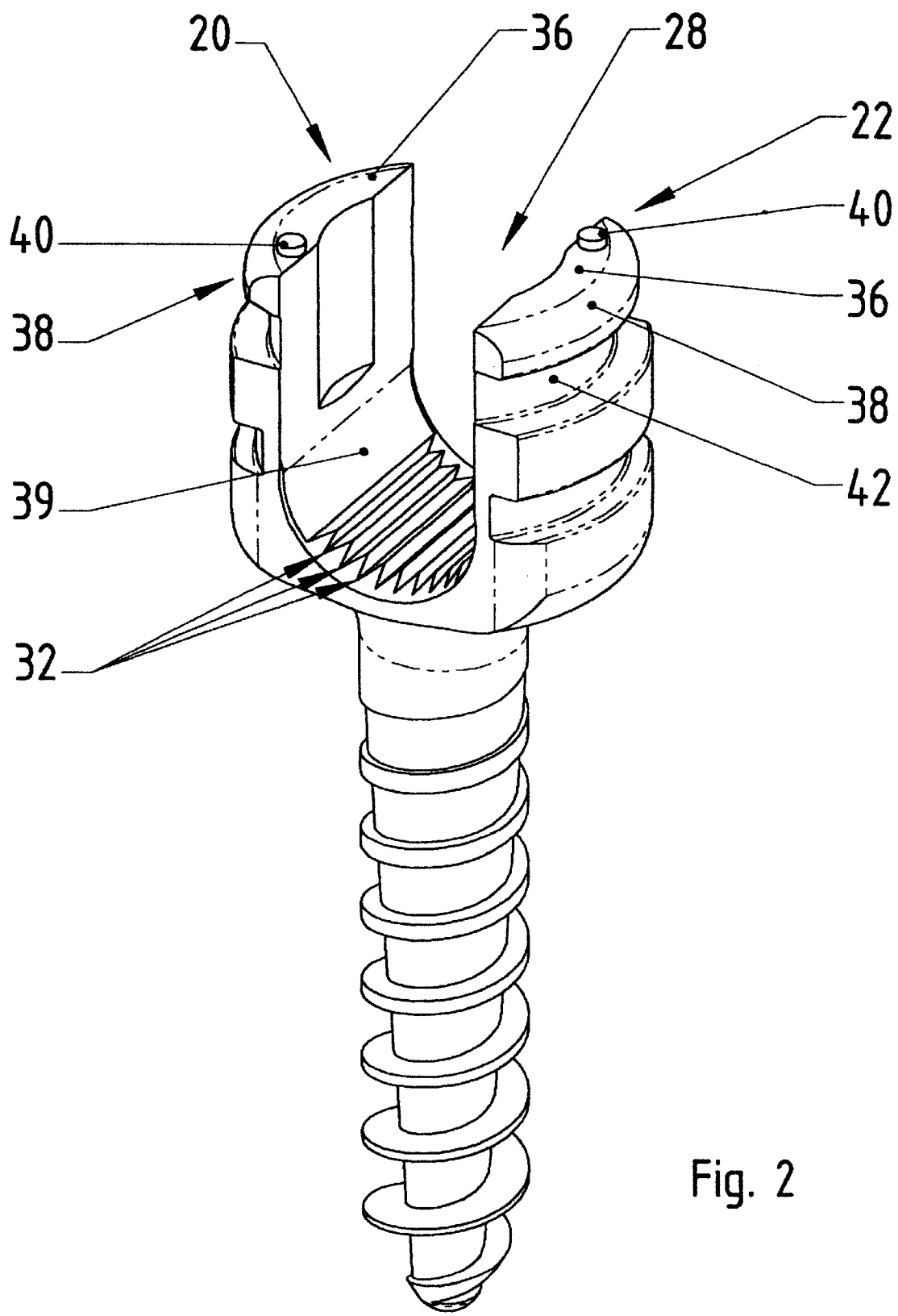
FIG. 2 shows a perspective view of the screw with removed nut.

FIG. 1 shows a particularly preferred embodiment in accordance with the invention, wherein the reference numeral 10 designates a bone screw. This bone screw 10 is connected to a correction rod 12. The bone screw 10 comprises a shaft 14 having a thread for screwing the bone screw 10 into a bone, a vertebrae or the like. The shaft 14 is conical and merges at its upper end into a forked head 16 in which the correction rod 12 is disposed. The forked head 16 is provided with a nut 18 which partially surrounds and closes the forked head 16 and secures the two legs 20 and 22 of the forked head 16 from being forced apart (FIG. 2). The upper side of the nut 18 comprises a central threaded bore 24 into which a set screw 26 can be screwed, thereby securely fixing the correction rod 12 in the forked head 16.

FIG. 2 clearly shows the groove 28 of the forked head 16 and several notches 32 extending in the longitudinal direction of the groove 28 are shown at the bottom 30 of the groove 28. These notches 32 engage in longitudinal grooves 34 in the correction rod 12 and thereby fix the correction rod 12 to prevent rotation thereof. The free ends 36 of the two legs 20 and 22 comprise radially outwardly extending projections 38 which form part of a bayonet joint. Two extensions 40 are provided at diametrally opposed sides of the projections 38 which protrude axially.

One groove 42 is disposed below each of the projections 38 which extend, like the projections 38, through the entire peripheral width of the legs 20 and 22.

Figure 3:
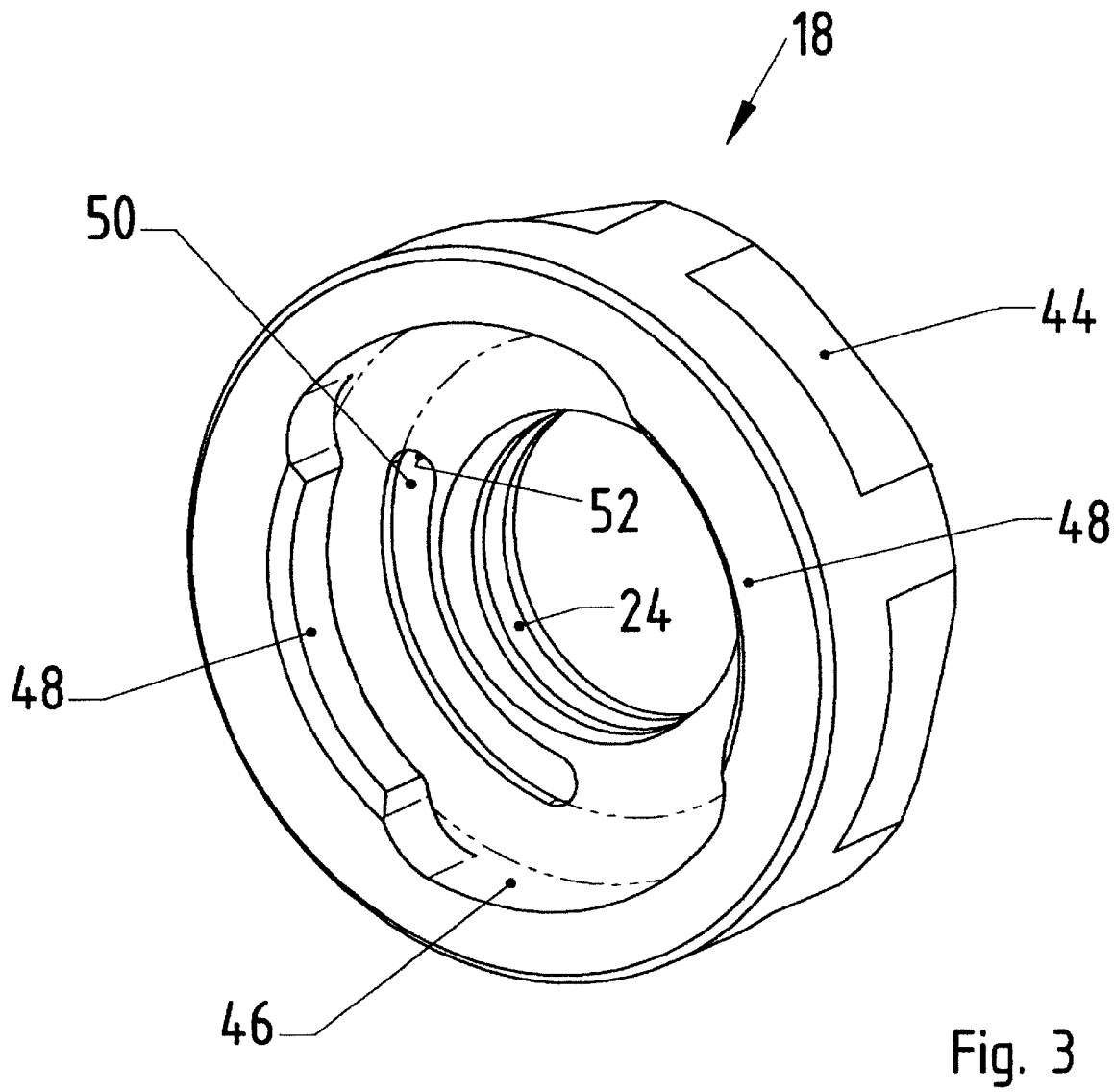
FIG. 3 shows a perspective view of the nut.

The outer circumference of the nut 18 shown in FIG. 3 comprises a tool engagement surface 44 which is formed as a hexagon. The inner side 46 of the nut 18 comprises two diametrally opposed noses 48 which project radially inwardly. These noses 48 extend over approximately 85° of the inner circumference. When the nut 18 is disposed on the forked head 16 (see FIG. 1), these noses 48 engage into associated grooves 42 below the projections 38 thereby forming a bayonet joint. A rotational limitation of the nut 18 is achieved via the extensions 40 which, when the nut 18 is disposed on the forked head 16, engage into a receiving groove 50 which is also provided on the inner side 46 of the nut 18. When the nut 18 is axially disposed onto the forked head 16, the extensions 40 engage into this receiving groove 50 to permit rotation of the nut 18 in one rotational direction only until the extensions 40 abut the groove wall 52. This ensures that the nut 18 and the bayonet joint can be closed merely in one rotational direction, namely in the mathematically "positive" direction. When the set screw 26 is screwed into the threaded bore 24 of the nut 18, the nut is held in this closed position and does not require any external support.

We claim:

1. A bone-screw system comprising:

a correction rod;

a bone-screw, said bone-screw having a threaded screw shaft, a forked head having a U-shaped receptacle between sideward fork legs for receiving said correction rod, said forked head defining a first bayonet joint connection structure at outer peripheral surfaces of said fork legs, said forked head having at least one axial protrusion integral with a free axial end of at least one of said fork legs; and a cap nut having a peripheral rim and an axially disposed bottom integral with that peripheral rim, said axially disposed bottom having a bottom wall thickness and a groove at an inner side of said bottom, said groove having a groove depth which is less than said bottom wall thickness to define an inwardly open bottom hole, said peripheral rim having a second bayonet joint connection structure at inner peripheral surfaces thereof, said second structure configured to avoid communication with all outer peripheral surfaces of said rim, wherein said second connection structure cooperates with said first connection structure and said groove accepts said axial protrusion to generate a bayonet joint connection when said cap nut is placed over said forked head and then rotated.

2. The bone-screw system of claim 1, wherein said first connection structure comprises radially outwardly protruding projections.

3. The bone-screw system of claim 1, wherein said first structure projections extend through a peripheral length of said fork legs.

4. The bone-screw system of claim 1, wherein said second connection structure comprises two radially inwardly projecting noses.

5. The bone-screw system of claim 4, wherein each of said noses extends through 20 degrees to 90 degrees of an inner periphery of said cap nut rim.

6. The bone-screw system of claim 1, wherein said cap nut groove cooperates with said axial protrusion to generate a bayonet connection stop.

7. The bone-screw system of claim 1, wherein, when said cap nut is engaged onto said forked head, a separation between a bottom of said U-shaped receptacle and said inner side of said cap nut bottom is larger than an inside transverse diameter of said U-shaped receptacle.

8. The bone-screw system of claim 1, wherein said cap nut bottom has a central threaded bore and further comprising a screw for engagement in said central threaded bore.

9. The bone-screw system of claim 8, wherein said screw is a set screw.

10. The bone-screw system of claim 9, wherein a screwing-in direction of said set screw corresponds to a closing direction of said bayonet joint.

11. The bone-screw system of claim 1, wherein an outer circumference of said cap nut defines a tool engagement surface.

12. The bone-screw system of claim 11, wherein said tool engagement surface is hexagonal.

* * * * *